US008586013B2

(12) United States Patent  
Bradshaw et al.

(10) Patent No.: US 8,586,013 B2  
(45) Date of Patent: *Nov. 19, 2013

(54) COMFORTABLE, LONG-WEARING, TRANSFER-RESISTANT COLORED COSMETIC COMPOSITIONS HAVING A NON-TACKY FEEL

(75) Inventors: Kimberly Bradshaw, Monmouth Junction, NJ (US); Hy Si Bui, Piscataway, NJ (US)

(73) Assignee: L'Oreal, Paris (FR)

( * ) Notice: Subject to any disclaimer, the term of this patent is extended or adjusted under 35 U.S.C. 154(b) by 73 days.

This patent is subject to a terminal disclaimer.

(21) Appl. No.: 12/981,839

(22) Filed: Dec. 30, 2010

(65) Prior Publication Data

US 2012/0171137 A1     Jul. 5, 2012

(51) Int. Cl.  
*A61Q 1/04* (2006.01)  
*A61Q 1/06* (2006.01)

(52) U.S. Cl.  
USPC ............................................ 424/64; 424/401

(58) Field of Classification Search  
None  
See application file for complete search history.

(56) References Cited

U.S. PATENT DOCUMENTS

| | | | |
|---|---|---|---|
| 6,964,773 B1 * | 11/2005 | Morrison | 424/401 |
| 7,842,285 B2 | 11/2010 | Lu et al. | |
| 7,879,316 B2 * | 2/2011 | Ferrari et al. | 424/64 |
| 2007/0093619 A1 | 4/2007 | Bui et al. | |
| 2008/0166309 A1 | 7/2008 | McDermott et al. | |
| 2008/0171006 A1 * | 7/2008 | Bui et al. | 424/64 |
| 2008/0305061 A1 | 12/2008 | Bui et al. | |

FOREIGN PATENT DOCUMENTS

WO    WO 2005/100444    10/2005

* cited by examiner

*Primary Examiner* — Jyothsna Venkat  
(74) *Attorney, Agent, or Firm* — L'Oreal USA

(57) ABSTRACT

The present invention is directed to an anhydrous composition which is long wearing and transfer resistant, while at the same time providing superior comfort, non-tacky feel and cushioning, the composition containing: (a) at least one silsesquioxane resin; (b) at least one polypropylsilsesquioxane wax substituted with alkyl units having at least 30 carbons; (c) at least one siloxysilicate resin; (d) at least one volatile solvent; (e) optionally, at least one non-volatile solvent; and (f) at least one colorant.

5 Claims, No Drawings

COMFORTABLE, LONG-WEARING, TRANSFER-RESISTANT COLORED COSMETIC COMPOSITIONS HAVING A NON-TACKY FEEL

BACKGROUND OF THE INVENTION

Cosmetic compositions used to make up a user's skin must be able to impart color with little to no transfer. They must also provide good wear properties. The transfer resistance and wear of cosmetic compositions are usually obtained through the use of film forming resins such as silicone film forming resins. While the use of silicone film forming resins in colored cosmetics is popular, one drawback associated with their use is that they tend to be brittle and flake off. This phenomenon results in the need to use a plasticizer, in combination with the resin, in order to render the resultant film more flexible and, hence, less susceptible to flake off and poor transfer resistance. Moreover, the resultant films formed by the resins are uncomfortable on human skin and, at times, have a tacky feel.

Therefore, it is an object of the present invention to provide a method and composition for making up skin in a manner which delivers a combination of long wear, transfer resistance, superior comfort and non-tacky feel.

BRIEF SUMMARY OF THE INVENTION

According to one embodiment of the present invention, there is provided an anhydrous composition which is long wearing and transfer resistant, while at the same time providing superior comfort, non-tacky feel and cushioning, the composition containing:

(a) at least one silsesquioxane resin;
(b) at least one polypropylsilsesquioxane wax substituted with alkyl units having at least 30 carbons;
(c) at least one siloxysilicate resin;
(d) at least one volatile solvent;
(e) optionally, at least one non-volatile solvent; and
(f) at least one colorant.

According to another aspect of the present invention, there is provided a method of making up skin involving applying onto the skin the above-disclosed composition.

It has been surprisingly discovered that the above-described cosmetic composition provides superior non-tacky feel, transfer resistance and comfort when applied onto a keratinous substrate.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Film former" or "film forming agent" as used herein means a polymer or resin that leaves a film on the substrate to which it is applied, for example, after a solvent accompanying the film former has evaporated, absorbed into and/or dissipated on the substrate.

"Transfer resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated by a "kiss" test. The "kiss" test may involve application of the composition to human keratin material such as hair, skin or lips followed by rubbing a material, for example, a sheet of paper, against the hair, skin or lips after expiration of a certain amount of time following application, such as 2 minutes after application. Similarly, transfer resistance of a composition may be evaluated by the amount of product transferred from a wearer to any other substrate, such as transfer from the hair, skin or lips of an individual to a collar when putting on clothing after the expiration of a certain amount of time following application of the composition to the hair, skin or lips. The amount of composition transferred to the substrate (e.g., collar, or paper) may then be evaluated and compared. For example, a composition may be transfer resistant if a majority of the product is left on the wearer's hair, skin or lips. Further, the amount transferred may be compared with that transferred by other compositions, such as commercially available compositions. In a preferred embodiment of the present invention, little or no composition is transferred to the substrate from the hair, skin or lips.

"Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to human hair, skin or lips and evaluating the color of the composition after an extended period of time. For example, the color of a composition may be evaluated immediately following application to hair, skin or lips and these characteristics may then be re-evaluated and compared after a certain amount of time. Further, these characteristics may be evaluated with respect to other compositions, such as commercially available compositions.

"Tackiness" as used herein refers to the adhesion between two substances. For example, the more tackiness there is between two substances, the more adhesion there is between the substances. To quantify "tackiness," it is useful to determine the "work of adhesion" as defined by IUPAC associated with the two substances. Generally speaking, the work of adhesion measures the amount of work necessary to separate two substances. Thus, the greater the work of adhesion associated with two substances, the greater the adhesion there is between the substances, meaning the greater the tackiness is between the two substances.

Work of adhesion and, thus, tackiness, can be quantified using acceptable techniques and methods generally used to measure adhesion, and is typically reported in units of force time (for example, gram seconds ("g s")). For example, the TA-XT2 from Stable Micro Systems, Ltd. can be used to determine adhesion following the procedures set forth in the TA-XT2 Application Study (ref: MATI/PO.25), revised January 2000, the entire contents of which are hereby incorporated by reference. According to this method, desirable values for work of adhesion for substantially non-tacky substances include less than about 0.5 g s, less than about 0.4 g s, less than about 0.3 g s and less than about 0.2 g s. As known in the art, other similar methods can be used on other similar analytical devices to determine adhesion.

"Waterproof" as used herein refers to the ability to repel water and permanence with respect to water. Waterproof properties may be evaluated by any method known in the art for evaluating such properties. For example, a mascara composition may be applied to false eyelashes, which may then be placed in water for a certain amount of time, such as, for example, 20 minutes. Upon expiration of the pre-ascertained amount of time, the false eyelashes may be removed from the water and passed over a material, such as, for example, a sheet of paper. The extent of residue left on the material may then be evaluated and compared with other compositions, such as, for example, commercially available compositions. Similarly, for example, a composition may be applied to skin, and the skin may be submerged in water for a certain amount of time. The amount of composition remaining on the skin after the pre-ascertained amount of time may then be evaluated and compared. For example, a composition may be waterproof if a majority of the product is left on the wearer, e.g., eyelashes, skin, etc. In a preferred embodiment of the present invention, little or no composition is transferred from the wearer.

"Substituted" as used herein, means comprising at least one substituent. Non-limiting examples of substituents include atoms, such as oxygen atoms and nitrogen atoms, as well as functional groups, such as amine groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

The compositions and methods of the present invention can comprise, consist of, or consist essentially of the essential elements and limitations of the invention described herein, as well as any additional or optional ingredients, components, or limitations described herein or otherwise useful.

The compositions of the present invention comprise at least one silsesquioxane resin.

Examples of silsesquioxane resins of the present invention are alkyl silsesquioxane resins which are silsesquioxane homopolymers and/or copolymers having an average siloxane unit of the general formula $R^1{}_n SiO_{(4-n)/2}$, wherein each $R_1$ is independently chosen from a hydrogen atom and a $C_1$-$C_{10}$ alkyl group, wherein more than 80 mole % of $R_1$ represent a $C_3$-$C_{10}$ alkyl group, n is a value of from 1.0 to 1.4, and more than 60 mole % of the copolymer comprises $R^1 SiO_{3/2}$ units.

Preferably, the silsesquioxane resin used is one where $R_1$ is a $C_1$-$C_{10}$, preferably a $C_1$-$C_4$ alkyl group, and more preferably a propyl group. A preferred silsesquioxane resin of the present invention is polypropylsilsesquioxane resin or t-propyl silsesquioxane resin. The t-propyl resin is commercially available from Dow-Corning under the tradename Dow Corning® 670 Fluid.

The silsesquioxane resin may be present in an amount ranging from about 1% to about 60% by weight, such as from about 3% to about 60% by weight, such as from about 5% to about 50% by weight, and such as from about 10% to about 40% by weight, all weights based on the weight of the composition as a whole.

The cosmetic compositions of the present invention also contain at least one polypropylsilsesquioxane wax substituted with alkyl units having at least 30 carbons.

Polypropylsilsesquioxane waxes, in general, have been disclosed in patent publication WO2005/100444, published on Oct. 27, 2005, the entire content of which is hereby incorporated by reference.

It should be noted, however, that not all polypropylsilsesquioxane waxes yield stable colored cosmetic emulsion products. More particularly, it has been found that only those polypropylsilsesquioxane waxes substituted with alkyl units having at least 30 carbons are stable.

The polypropylsilsesquioxane wax comprises at least 40 mole % of siloxy units having the formula $(R_2R'SiO_{1/2})_x (C_3H_7SiO_{3/2})_y$, where x and y have a value of 0.05 to 0.95, R is an alkyl group having from 1 to 8 carbon atoms, and R' is a monovalent hydrocarbon having 30 to 40 carbon atoms and greater. As used herein, x and y represent the mole fraction of $(R_2R'SiO_{1/2})$ and $(C_3H_7SiO_{3/2})$ siloxy units relative to each other present in the polypropylsilsesquioxane wax. Thus, the mole fraction of $(R_2R'SiO_{1/2})$ and $(C_3H_7SiO_{3/2})$ siloxy units each can independently vary from 0.05 to 0.95. Preferably R is a methyl, and R' is an alkyl having at least 30 carbons, available from Dow Corning.

Typically, the value of x is 0.05 to 0.95, or alternatively, 0.2 to 0.8, the value of y is 0.05 to 0.95, alternatively 0.2 to 0.8. However, the combination of $(R_2R'SiO_{1/2})$ and $(C_3H_7SiO_{3/2})$ siloxy units present must total at least 40 mole %, alternatively 60 mole %, or alternatively 90 mole % of all siloxy units present in the polypropylsilsesquioxane wax.

The number average molecular weight of the polypropylsilsesquioxane wax substituted with alkyl units having at least 30 carbons typically ranges from about 750 to about 10,000, such as from about 1,000 to about 5,000.

A particularly preferred polypropylsilsesquioxane wax for use in the present invention is a C30-45 ALKYLDIMETHYLSILYL POLYPROPYLSILSESQUIOXANE commercially available from DOW CORNING under the tradename SW-8005 C30 Resin Wax.

The polypropylsilsesquioxane wax substituted with alkyl units having at least 30 carbons is generally present in the cosmetic composition of the present invention in an amount ranging from about 0.1% to about 10% by weight; such as from about 0.5% to about 5% by weight; such as from about 0.75% to about 2.5% by weight, all weights being based on the weight of the composition as a whole.

The cosmetic compositions of the present invention further comprise at least one siloxysilicate. One non-limiting example of a siloxysilicate in accordance with the present invention is trimethylsiloxysilicate, which may be represented by the following formula:

$$[(CH_3)_3XSiXO]_xX(SiO_{4/2})_y$$

wherein x and y may, for example, range from 50 to 80. Such siloxysilicates are commercially available from General Electric and Dow Corning under the tradename Resin MQ®.

The at least one siloxysilicate is generally present in the cosmetic composition of the present invention in an amount ranging from about 1% to about 30% by weight; such as from about 5% to about 25% by weight; such as from about 10% to about 20% by weight, all weights being based on the weight of the composition as a whole.

According to certain embodiments of the present invention, the ratio by weight of the least one silsesquioxane resin to the at least one siloxysilicate is greater than 1, such as from about 3.0:1.0, from about 2.5:1.0, from about 2.3:1, 2.0:1, and from about 1.5:1.0.

According to preferred embodiments of the present invention, the ratio by weight of the least one silsesquioxane resin to the at least one siloxysilicate is from about 1.5:1.0, and most preferably, from about 2.3:1.0.

The composition of the invention also contains at least one volatile solvent.

The expression "volatile solvent" means any non-aqueous medium capable of evaporating on contact with the skin or the lips in less than one hour at room temperature and atmospheric pressure.

Examples of suitable volatile solvents include volatile hydrocarbon-based oils such as, for example, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, isohexadecane, and for example, the oils sold under the trade names of Isopar or Permethyl, the $C_8$ to $C_{16}$ branched esters such as isohexyl or isodecyl neopentanoate, alcohols, and their mixtures. Preferably, the volatile hydrocarbon-based oils have a flash point of at least 40° C.

Examples of volatile hydrocarbon-based oils include, but are not limited to those given in Table 1 below.

TABLE 1

| Compound | Flash Point (° C.) |
| --- | --- |
| Isododecane | 43 |
| Isohexadecane | 102 |
| Isodecyl neopentanoate | 118 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

The volatile solvent may also be chosen from volatile silicone oils, which may be linear or cyclic, having a viscosity, at room temperature, of less than or equal to 6 cSt, and having from 2 to 7 silicon atoms, optionally substituted with alkyl or alkoxy groups of 1 to 10 carbon atoms.

Examples of suitable volatile silicone oils include, but are not limited to, those listed in Table 2 below.

TABLE 2

| Compound | Flash Point (° C.) | Viscosity (cSt) |
| --- | --- | --- |
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane(L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |
| PDMS DC 200 (5 cSt) from Dow Corning | 134 | 5 |
| PDMS DC 200 (3 St) from Dow Corning | 102 | 3 |

The at least one volatile solvent is generally present in the cosmetic composition of the present invention in an amount ranging from about 15% to about 70% by weight; such as from about 25% to about 50% by weight; such as from about 30% to about 40% by weight, all weights being based on the weight of the composition as a whole.

Examples of suitable non-volatile solvents include, but are not limited to, polar oils and non-polar oils such as:

hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;

synthetic oils or esters of formula $R_5COOR_6$ in which $R_5$ represents a linear or branched higher fatty acid residue containing from 1 to 40 carbon atoms, including from 7 to 19 carbon atoms, and $R_6$ represents a branched hydrocarbon-based chain containing from 1 to 40 carbon atoms, including from 3 to 20 carbon atoms, and also including, for example, octyldodecyl neopentanoate, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

synthetic ethers containing from 10 to 40 carbon atoms;

$C_8$ to $C_{26}$ fatty alcohols, for instance oleyl alcohol; and mixtures thereof.

Further, examples of non-volatile oils that may be used in the present invention include, but are not limited to, non-polar oils such as branched and unbranched hydrocarbons and hydrocarbon waxes including polyolefins, in particular Vaseline (petrolatum), paraffin oil, squalane, squalene, hydrogenated polyisobutene, hydrogenated polydecene, polybutene, mineral oil, pentahydrosqualene, and mixtures thereof.

Examples of non-volatile solvents also include non-volatile silicones such as dimethicone fluids having viscosity values of equal to or greater than 300 cst. The preferred non-volatile solvent in the present invention is pentaphenyldimethicone, also known as trimethyl pentaphenyl trisiloxane, commercially available from Dow Corning as DC555.

The at least one non-volatile solvent may be present in the cosmetic composition of the present invention in an amount ranging from about 1% to about 50% by weight; such as from about 5% to about 40% by weight; such as from about 10% to about 30% by weight, all weights being based on the weight of the composition as a whole.

The cosmetic compositions of the present invention also contain at least one cosmetically acceptable colorant such as a pigment or dyestuff. Examples of suitable pigments include, but are not limited to, inorganic pigments, organic pigments, lakes, pearlescent pigments, irridescent or optically variable pigments, and mixtures thereof. A pigment should be understood to mean inorganic or organic, white or colored particles. Said pigments may optionally be surface-treated within the scope of the present invention but are not limited to treatments such as silicones, perfluorinated compounds, lecithin, and amino acids.

Representative examples of inorganic pigments useful in the present invention include those selected from the group consisting of rutile or anatase titanium dioxide, coded in the Color Index under the reference CI 77,891; black, yellow, red and brown iron oxides, coded under references CI 77,499, 77, 492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

Representative examples of organic pigments and lakes useful in the present invention include, but are not limited to, D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7

(CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430) and the dye or lakes based on cochineal carmine (CI 75,570) and mixtures thereof.

Representative examples of pearlescent pigments useful in the present invention include those selected from the group consisting of the white pearlescent pigments such as mica coated with titanium oxide, mica coated with titanium dioxide, bismuth oxychloride, titanium oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof.

The precise amount and type of colorant employed in the compositions of the present invention will depend on the color, intensity and use of the cosmetic composition and, as a result, will be determined by those skilled in the art of cosmetic formulation. However, one preferred amount of colorant for use in the present invention is from about 0.5% to about 7.5%, based on the weight of the composition.

Additives/Auxiliary Agents

The compositions of the present invention may further comprise at least one cosmetically or dermatologically acceptable additive such as a thickener, a film former, a plasticizer, an antioxidant, an essential oil, a preserving agent, a fragrance, a filler, a pasty fatty substance, a waxy fatty substance, a neutralizing agent, and a polymer, and cosmetically active agents and/or dermatological active agents such as, for example, emollients, moisturizers, vitamins, essential fatty acids and medicaments.

Fillers that may be used in the compositions of the invention include, for example, silica powder; talc; polyamide particles and especially those sold under the name Orgasol by the company Atochem; polyethylene powders; microspheres based on acrylic copolymers, such as those based on ethylene glycol dimethacrylate/lauryl methacrylate copolymer sold by the company Dow Corning under the name Polytrap; expanded powders such as hollow microspheres and especially the microspheres sold under the name Expancel by the company Kemanord Plast or under the name Micropearl F 80 ED by the company Matsumoto; powders of natural organic materials such as crosslinked or noncrosslinked corn starch, wheat starch or rice starch, such as the powders of starch crosslinked with octenyl succinate anhydride, sold under the name Dry-Flo by the company National Starch; silicone resin microbeads such as those sold under the name Tospearl by the company Toshiba Silicone; clays (bentone, laponite, saponite, etc.); and mixtures thereof.

The fillers may be present in the composition of the invention in an amount ranging from about 0.1% to about 50% by weight, such as from 0.5% to about 30% by weight, and such as from about 1% to about 20% by weight, all weights based on the weight of the composition as a whole.

It has been surprisingly discovered that the composition of the present invention is transfer resistant and long wearing, and at the same time, provides superior comfort, non-tacky feel and cushioning.

It has also been surprisingly discovered that the association of a silsesquioxane resin, a polypropylsilsesquioxane wax substituted with alkyl units having at least 30 carbons, and a siloxysilicate resin, in the presence of a volatile solvent results in the formation of an anhydrous composition having long wearing, transfer resistant properties on skin, such as the lips and the face, while providing superior comfort, a non-tacky feel and cushioning to the skin. Moreover, the presence of a non-volatile solvent to the composition can result in a composition that imparts additional shine.

The compositions of the present invention are useful as compositions for making up the skin. These compositions include lipstick, eyeshadow and mascara products.

The present invention will be better understood from the examples which follow, all of which are intended for illustrative purposes only.

EXAMPLES

A lip composition in accordance with the present invention was formulated. The ingredients employed are found in Table 1, below.

Comparative Data:

| Ingredients | A | B | C | D | E |
|---|---|---|---|---|---|
| T-PROPYL RESIN ratio/MQ | 30:70 | 40:60 | 50:50 | 60:40 | 70:30 |
| MQ RESIN/TRIMETHYLSILOXYSILICATE/SR 1000 | 26.5 | 24 | 20.5 | 15.98 | 11.37 |
| POLYPROPYLSILSESQUIOXANE (75%) AND ISODODECANE (25%) | 15.16 | 21.3 | 27.33 | 32 | 35.33 |
| C30-45 ALKYLDIMETHYLSILYL POLYPROPYLSILSESQUIOXANE (and) PARAFFIN/DOW CORNING SW-8005 C30 RESIN WAX | 1 | 1 | 1 | 1 | 1 |
| ISODODECANE | 26.5 | 24 | 20.5 | 15.98 | 11.37 |
| BENTONE GEL/DISTEARDIMONIUM HECTORITE (and) PROPYLENE CARBONATE/BENTONE GEL ISD V | 25 | 25 | 25 | 25 | 25 |
| LAUROYL LYSINE/AMIHOPE LL | 1.5 | 1.5 | 1.5 | 1.5 | 1.5 |
| RED 7(CI 15850)/UNIPURE RED LC 3079 OR | 3.1 | 3.1 | 3.1 | 3.1 | 3.1 |

-continued

| Ingredients | A | B | C | D | E |
|---|---|---|---|---|---|
| MICA (CI: 77019) | 1.14 | 0 | 0.97 | 0 | 1.14 |
| FRAGRANCE/PARFUM/ | 0.1 | 0.1 | 0.1 | 0.1 | 0.1 |
| Total | 100 | 100 | 100 | 100 | 100 |
| WEAR EVALUATION | MODERATE to GOOD | MODERATE to GOOD | MODERATE to GOOD | MODERATE to GOOD | MODERATE to GOOD |
| STRETCH BAND EVALUATION FOR FILM FLEXIBILITY | 4 | 3 | 2 | 1 | 0 |

Stretch Band Evaluation:

Each composition in the table above was applied on the surface of an elastic flat stretch band using an applicator and by spreading the product evenly going in a clockwise direction from the point of application in order to form a film on the band. Each band was then placed on a heating table set at 37 C for approximately 25 to 30 minutes. The bands were then removed from the heating table and stretched evenly. The flexibility of the films was evaluated according to the stretch band evaluation scores ranging from 0-5, with 0 being most flexible with no cracking of the film, 5 being not very flexible and accompanied by cracking of the film.

One of ordinary skill in the art would expect the addition of a silicone wax to the above formulation would result in a decrease in wear/transfer resistance, as waxes are known in the industry to negatively impact these properties. The inventors have surprisingly and unexpectedly discovered, however, that based on the results above, the inventive compositions demonstrated moderate to good wear/transfer resistance properties, while at the same time, increased comfort level on the wearer's lips and providing a non-tacky feel. Moreover, at certain ratios by weight of the t-propyl resin to the MQ resin, the compositions D and E had exhibited improved flexibility of the film formed upon application on a substrate.

Procedure:

Phase A: In a beaker, 11.37% of MQ resin was combined with 11.37% of Isododecane and the combination was mixed using a propeller at about 350 rpm until the MQ resin was completely dissolved in the isododecane. Next, 35.33% of the t-propyl resin in isododecane was added and mixing was continued. Lauroyl lysine and pigments were then added and mixing was continued until the Lauroyl Lysine was dissolved and the pigments were wet. Next, 25% of Bentone Gel was added to the mixture and mixing was continued until a smooth creamy texture was observed. The resulting mixture was then transferred to the disconti mill and ground until the pigments were completely dispersed.

Phase B:

Phase A was removed from the disconti mill and transferred to a beaker. The t-propyl resin wax was added and mixed in at about 60 c until the wax was completely dissolved. Mica, fillers and fragrance were then added. The temperature source was then turned off to allow the batch to cool down to around 60 C. The batch was weighed to check for weight loss. Any weight loss was offset by adding isododecane.

The complete process was closely monitored and performed under closed kettle conditions to reduce the loss of isododecane.

What is claimed:

1. A composition comprising:
    (a) from about 10% to about 40% by weight of a polypropylsilsesquioxane resin;
    (b) from about 0.75% to about 2.5% by weight of $C_{30-45}$ alkyldimethylsilyl polypropylsilsesquioxane;
    (c) from about 10% to about 20% by weight of a trimethylsiloxysilicate;
    (d) from about 30% to about 40% by weight of isododecane;
    (e) optionally, at least one non-volatile solvent; and
    (f) from about 0.5% to about 7.5% by weight of at least one colorant;
    said composition being anhydrous; wherein the ratio by weight of (a) to (c) is about 1.5:1.0 to about 2.3:10, all weights being based on the total weight of the composition.

2. The composition of claim 1 wherein (e) is present in the composition in an amount of from about 10% to about 30% by weight, based on the weight of the anhydrous composition.

3. A composition comprising:
    (a) about 35.33% by weight of a polypropylsilsesquioxane resin selected from polypropylsilsesquioxane(75%)/isododecane(25%);
    (b) about 1% by weight of $C_{30-45}$ alkyldimethylsilyl polypropylsilsesquioxane
    (c) about 11.37% by weight of a trimethylsiloxysilicate;
    (d) about 11.37% by weight of isododecane;
    (e) optionally, at least one non-volatile solvent; and
    (f) from about 0.5% to about 7.5% by weight of at least one colorant;
    said composition being anhydrous; wherein the ratio by weight of (a) to (c) is about 2.3:1.0, all weights being based on the total weight of the composition.

4. A composition comprising:
    (a) about 32% by weight of a polypropylsilsesquioxane resin selected from polypropylsilsesquioxane(75%)/isododecane(25%);
    (b) about 1% by weight of $C_{30-45}$ alkyldimethylsilyl polypropylsilsesquioxane;
    (c) about 15.98% by weight of a trimethylsiloxysilicate;
    (d) about 15.98% by weight of isododecane;
    (e) optionally, at least one non-volatile solvent; and
    (f) from about 0.5% to about 7.5% by weight of at least one colorant;
    said composition being anhydrous; wherein the ratio by weight of (a) to (c) is about 1.5:1.0, all weights being based on the total weight of the composition.

5. A method of making up a keratinous substrate comprising applying onto the keratinous substrate an anhydrous composition containing:
    (a) from about 10% to about 40% by weight of a polypropylsilsesquioxane resin;
    (b) from about 0.75% to about 2.5% by weight of $C_{30-45}$ alkyldimethylsilyl polypropylsilsesquioxane;
    (c) from about 10% to about 20% by weight of a trimethylsiloxysilicate;

(d) from about 30% to about 40% by weight of isododecane;
(e) optionally, at least one non-volatile solvent; and
(f) from about 0.5% to about 7.5% by weight of at least one colorant;
said composition being anhydrous; wherein the ratio by weight of (a) to (c) is about 1.5:1.0 to about 2.3:10, all weights being based on the total weight of the composition.

* * * * *